United States Patent [19]
Bills et al.

[11] Patent Number: 5,352,800
[45] Date of Patent: Oct. 4, 1994

[54] PROCESS FOR THE PRODUCTION OF A NOVEL ENDOTHELIN ANTAGONIST

[75] Inventors: Gerard F. Bills, Cranford; Michael A. Goetz, Fanwood; Robert A. Giacobbe, Lavallette, all of N.J.; Lucia Herranz, Madrid, Spain; E. Tracy Turner Jones, Solana Beach, Calif.; Fernando Pelaez, Madrid, Spain; Yu L. Kong, Edison, N.J.; Sheo B. Singh, Edison, N.J.; Siobhan Stevens-Miles, Jersey City, N.J.

[73] Assignee: Merck & Co., Inc., Rahway, N.J.

[21] Appl. No.: 29,745

[22] Filed: Mar. 11, 1993

[51] Int. Cl.$^5$ ............................................. C07D 207/273
[52] U.S. Cl. .................................... 548/539; 435/121; 435/911
[58] Field of Search .................................... 548/539

[56] References Cited

U.S. PATENT DOCUMENTS

| | | | |
|---|---|---|---|
| 5,082,838 | 1/1992 | Naka et al. | 514/211 |
| 5,114,918 | 5/1992 | Ishikawa et al. | 514/11 |
| 5,187,195 | 2/1993 | Oohata et al. | 514/510 |

FOREIGN PATENT DOCUMENTS

| | | |
|---|---|---|
| 0436189A1 | 10/1990 | European Pat. Off. . |
| 0457195-A2 | 11/1991 | European Pat. Off. . |
| 0460679-A2 | 12/1991 | European Pat. Off. . |
| 0496452-A1 | 7/1992 | European Pat. Off. . |
| 0510526-A1 | 10/1992 | European Pat. Off. . |
| 0526642-A1 | 2/1993 | European Pat. Off. . |
| 0526708-A1 | 2/1993 | European Pat. Off. . |
| WO92/15321 | 9/1992 | PCT Int'l Appl. . |
| WO92/20706 | 11/1992 | PCT Int'l Appl. . |
| 2259450 | 3/1993 | United Kingdom . |

Primary Examiner—Joseph Paul Brust
Attorney, Agent, or Firm—Valerie J. Camara; Mark R. Daniel; Joseph F. DiPrima

[57] ABSTRACT

Fermentation processes for the production of a compound of the Structural Formula I The compound of Structural Formula I has been shown to have endothelin antagonist activity and is therefore useful in treating cardiovascular disorders, such as hypertension, congestive heart failure, postischemic renal failure vasospasm, cerebral and cardia ischemia, myocardial infarction inflammatory diseases, Raynaud's disease, endotoxin shock and asthma.

1 Claim, No Drawings

PROCESS FOR THE PRODUCTION OF A NOVEL ENDOTHELIN ANTAGONIST

SUMMARY OF THE INVENTION

This invention is concerned with a fermentation process useful in the production of an endothelin antagonist. The fermentation process employs one of two possible fungal strains. These fungal strains were obtained from dead grass culms collected in New Mexico (MF5810) and from leaf litter of *Juniperus deppeana* (MF5811) collected in Texas. Both of these fungal strains were separately fermented under the appropriate fermentation conditions and methyl ethyl ketone (MEK) extracts were shown to be active in the endothelin binding assay.

This invention is concerned with a non-peptidic endothelin receptor antagonist and their method of use. The compound of the present invention is a therapeutic agent particularly useful for the treatment of asthma, hypertension, pulmonary hypertension, arteriosclerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynauc's disease, inflammatory bowel diseases, including Crohn's disease and ulcerative colitis, as well as other inflammatory diseases, or endotoxic shock caused by or associated with endothelin.

BACKGROUND OF THE INVENTION

Endothelin is a 21-amino acid peptide produced by endothelial cells. The peptide is secreted not only by endothelial cells but also by tracheal epithelial cells or from kidney cells. Endothelin (ET-1) has a potent vasoconstrictor effect. The vasoconstricting effect is caused by the binding of endothelin to its receptor on the vascular smooth muscle cells.[1,2,3]

Endothelin-1 (ET-1) is one of three recently identified potent vasoconstricting peptides which also includes endothelin-2 (ET-2) and endothelin-3 (ET-3) which differ from ET-1 by two and six amine acids, respectively.[4]

Increased levels of endothelin are found in the blood of patients with essential hypertension, acute myocardial infarction, pulmonary hypertension, Raynaud's disease or atherosclerosis or in the washing fluids of the respiratory tract of patients with asthma as compared to normal levels.[5,6,7,8]

An experimental model of a cerebral vasespasm and a second model of acute renal failure have led to the conclusion that endothelin is one of the mediators causing cerebral vasespasms following a subarachnoid hemorrhage, and renal failure.[9,10]

Endothelin was also found to control the release of many physiological substances such as renin, atrial natriuretic peptide, endothelium-derived relaxing factor (EDRF), thromboxane A2,[14,] prostacyclin, norepinephrine, angiotensin II and substance P.[11,12,13,14,15,16] Further, endothelin causes contraction of the smooth muscle of gastrointestinal tract and the uterine smooth muscle.[17,18,19] Endothelin has also been shown to promote the growth of rat vascular smooth muscle cells which would suggest a possible relevance to arterial hypertrophy.[20]

Endothelin receptors are present in high concentration not only in the peripheral tissues but also in the central nervous system, and cerebral administration of endothelin has been shown to induce behavioral changes in animals, suggesting endothelin plays an important role for controlling neural functions.[21]

Endotoxin has been shown to promote the release of endothelin. This finding has suggested that endothelin is one important mediator for endotoxin-induced diseases.[22,23]

A study has shown that when cyclosporin added to a renal cell culture increased endothelin secretion is observed.[24] Another study has shown that when cyclosporin was admininstered to rats, a decrease in the glomerular filtration rate and an increase in the blood pressure were observed, in association with a remarkable increase in the circulating endothelin level. This cyclosporin-induced renal failure can be suppressed by the administration of endothelin antibody.[25] These studies suggest that endothelin is significantly involved in the pathogenesis of cyclosporin-induced diseases.

A recent study in patients with congestive heart failure demonstrated a good correlation between the elevated levels of endothelin in the plasma and the severity of the disease.[26]

Substances which specifically inhibit the binding of endothelin to its receptor are believed to antagonize the above mentioned physiological activities of endothelin and thereby would be expected to be a useful method of treatment for a person in need of such treatment. The present invention discloses potent non-peptidic endothelin antagonists.

Endothelin is an endogenous substance which directly or indirectly (through the controlled release of various other endogenous substances) induces sustained contraction of vascular or non-vascular smooth muscles and its excess production or excess secretion is believed to be one of the pathogeneses for hypertension, pulmonary hypertension, Raynaud's disease, bronchial asthma, acute renal failure, myocardial infarction, angina pectoris, arteriosclerosis, cerebral vasospasm and cerebral infarction.

The novel compound of the present invention is useful as a non-peptidic endothelin antagonist, which have not been disclosed in any issued patents or any known patent applications. Fujisawa in European Patent Application EP 457,195, Banyu in EP 436, 189 and 460,679, and Takeda in Patent Cooperation Treaty International Publication No. WO 91/13089 have applications disclosing linear and cyclic peptidic compounds as endothelin antagonists. Fujisawa has also disclosed anthraquinone derivatives produced by a fermentation process using Streptomyces sp. No. 89009 in EP 405,421.

A Roussel-Uclaf European Patent Application (EP 498,723) disclosed a series of substituted (1,4-quinolinoxy)methylbiphenylcarboxylic acids as both endothelin antagonists and angiotensin H antagonists. A patent from Roche (EP 510,526) has also appeared claiming endothelin antagonists properties of a series of N-(4-pyrimidinyl)benzenesulfonamides.

REFERENCES

1 Nature, 332, 411–415 (1988).
2 FEBS Letters, 231, 440–444 (1988).
3 Biochem. Biophys. Res. Commun. 154, 868–875 (1988).
4 TiPS, 13, 103–108, March 1992.
5 Japan J. Hypertension 12, 79 (1989).
6 J. Vascular Medicine Biology, 2, 207 (1990).
7 J. Am. Med. Association, 264, 2868 (1990).

8 The Lancet, ii, 207 (1990) and The Lancet, ii, 747–748 (1989).
9 Japan. Soc. Cereb. Blood Flow & Metabol. 1, 73 (1989).
10 J. Clin. Invest., 83, 1762–1767 (1989).
11 Biochem. Biophys. Res. Comm. 152, 1164–1168 (1988).
12 Biochem. Biophys. Res. Comm. 155, 167–172 (1989).
13 Proc. Natl. Acad. Sci. U.S.A., 85, 9797–9800 (1989).
14 J. Cardiovasc. Pharmacol., 13, 589–592 (1989).
15 Japan. J. Hypertension 12, 76 (1989).
16 Neuroscience Letters, 102, 179–184 (1989).
17 FEBS Letters, 247, 337–340 (1989).
18 Eur. J. Pharmacol. 154, 227–228 (1988).
19 Biochem. Biophys. Res. Commun., 159, 317–323 (1989).
20 Atherosclerosis, 78, 225–228 (1989).
21 Neuroscience Letters, 97, 276–279 (1989).
22 Biochem. Biophys. Res. Commun. 161, 1220–1227 (1989).
23 Acta. Physiol. Scand., 137, 317–318 (1989).
24 Eur. J. Pharmacol., 180, 191–192 (1990).
25 Kidney Int. 37, 1487–1491 (1990).
26 Mayo Clinic Proc., 67, 719–724 (1992).

DETAILED DESCRIPTION OF THE INVENTION

The product of this invention is the compound represented by structural formula I:

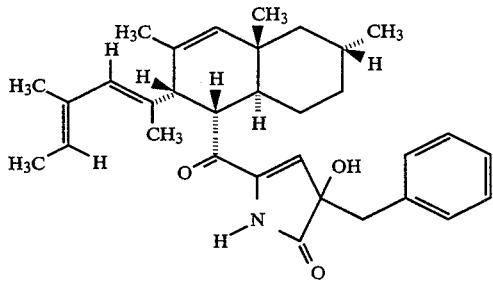

The process of this invention comprises fermentation of the fungal strain MF5810 or MF5811 in a nutrient medium and isolation of the compound of structural formula I in a conventional manner.

A biologically pure sample of each of the two fungal strains useful in the process - MF5810 and MF5811- are currently available in the permanent culture collection of the American Type Culture Collection, 12301 Parklawn Drive in Rockville Md. and are available under the accession numbers ATCC 74201 and 74202, respectively, as of Dec. 29, 1992.

The following is a description of the colony characteristics and diagnostic microscopic features of the MF5810 and MF5811 strains.

MF5810 (ATCC 74201)

Isolated from surface-sterilized culms of an unidentified dead grass, near Hope, Eddy Co., New Mexico.

Colonies on Czapek yeast autolyzate agar ($K_2HPO_4$ 1.0 g; yeast extract 5 g; sucrose 30 g; agar 15 g; $NaNO_3$ 3 g; KCl 0.5 g; $MgSO_4.7H_2O$ 0.5 g; $FeSO_4.7H_2O$ 0.01 g in 1000 ml $H_2O$) at 25° C., 12 hr photoperiod, growing moderately fast, attaining a diameter of 65 mm in one week, cottony to felty, zonate, with minute drops of vinaceous exudate over inner fourth of colony, also with minute clear drops over outer three-fourths of colony, with margin minutely fimbriate, white at first, soon developing pale vinaceous zones in response to photoperiod, Pale Purplish Vinaceous (capitalized color names from Ridgway, R. 1912. Color Standards and Nomenclature, published by the author, Washington, D.C.), Light Purplish Vinaceous. Reverse cream color to pale vinaceous. Odor sweet or fragrant. At 37° C. in the dark, growing extremely fast, >90 mm in one week, felty, with abundant droplets of clear exudate, white with a faint vinaceous cast, uniformly cream-color in reverse. No growth was observed at 55° C.

Colonies growing moderately fast on Barnett's oak wilt agar (Barnett, H. L. 1953. Isolation and identification of the oak wilt fungus. West Virginia Agricultural Experiment Station Bulletin 359T: 1-15.), 25° C., 12 hr photoperiod, attaining 67 mm in one week, downy, translucent, with margin finely fimbriate. Reverse hyaline, translucent. Odor slightly fragrant. After 3–4 weeks, dull greenish brown hyphal aggregations resembling sclerotia or protoperithecia develop submerged in the agar. These structures are 60–100 μm in diameter, sterile, with hyphae arranged in a textura intricata.

Colonies on Spezieller Nährstoffarmer agar (Nirenberg, H. 1976. Untersuchungen über die morpholoigische und biologische Differenzierung in der Fusariuru-Sektion Liseola. Mitt. Biol. Bund. Land- und Forstw. Berlin-Dahleru 169: 1–117) growing moderately fast, attaining 67 mm in one week, downy, translucent, with ruargin finely fimbriate. Reverse hyaline, translucent. Odor slightly fragrant.

After 3–4 weeks on Spezieller Nährstoffarmer agar with 1 cm filter paper squares placed on the surface, dull green hyphal aggregations resembling protoperithecia, similar to those formed on oak wilt agar, develop around the edges of the filter paper.

Conidiogenous cells enteroblastic, phialidic, simple, occasionally with a perpendicular branch, determinate, up to 9 μm tall X 2 μm, solitary, generally scattered on aerial hyphae. Conidia aseptate, ellipsoidal, hyaline, smooth, thin-walled, 2–3.5×1.–2.5 μm, adhering in moist clusters at apex of conidiogenous cells. Hyphae branched, septate, often with dull vinaceous pigment granules or incrustations.

MF5811 (ATCC 74202)

Isolated from leaf litter of Jupinerus deppeana, along highway 62/180, between Salt Flat and Pine Springs, Culberson Co., Texas.

Colonies on Czapek yeast autolyzate agar, at 25° C., 12 hr photoperiod, growing moderately fast, attaining a diameter of 83 mm in one week, cottony to woolly, downy towards inoculation point because in older regions of the colony the hyphae tend to collapse, zonate, middle third of mycelial mat covered with dark vinaceous droplets of exudate, with margin even to minutely fimbriate, white at margin, soon pale vinaceous to vinaceous, Pale Vinaceous, Purplish Vinaceous, Deep Vinaceous, Dark Vinaceous, pigmentation more or less coinciding with exudations from surface of colony. Reverse cream colored to deep vinaceous in age, ranging from Light Purplish Vinaceous to Vinaceous-Purple, Dark Vinaceous-Purple, or Corinthian Purple. Odor sweet or fragrant. At 37° C. in the dark, growing extremely fast, >90 mm in diameter in one week, cottony to felty with abundant exudate sublacunose due to accumulation of droplets of exudate, color similar to that at 25° C., but with more intense vinaceous colors. No growth was observed at 55° C.

Colonies growing moderately fast on Barnett's oak wilt agar, 25° C., 12 hr photoperiod, attaining a diameter of 65 mm in one week, downy, translucent or with pale yellow pigmentation exuded into the agar near point of inoculation, rarely with a few vinaceous exudate droplets on aerial hyphae. Reverse translucent. As similar to strain MF5810, after 3–4 weeks, dull greenish brown hyphal aggregations resembling sclerotia or protoperithecia develop submerged in the agar. These structures are 60–100 μm in diameter, sterile, with hyphae arranged in a textura intricata.

Colonies on Spezieller Nährstoffarmer Agar growing moderately fast, attaining 64 mm in one week, downy, translucent, with margin finely fimbriate. Reverse hyaline, transluent, with margin finely fimbriate. Reverse hyaline, translucent. Odor slightly fragrant. As similar to MF5810, after 3–4 weeks on Spezieller Nährstoffarmer agar with 1 cm filter paper squares placed on the surface, dull green hyphal aggregations resembling protoperithecia develop around the edges of the filter paper.

Conidiogenous cells enteroblastic, phialidic, simple, rarely with one right angle, branch determinate, up to 9 μm tall×2 μm, usually solitary, generally scattered on aerial hyphae. Conidia aseptate, ellipsoidal, hyaline, smooth, thin-walled, 2–3.5×1–2.5 μm, adhering in moist clusters at apex of conidiogenous cells. Hyphae branched, septate, often accumulating dull vinaceous pigment granules or incrustations.

Both of the above-described strains appear to be the same morphological species because of their similarity in quality of pigmentation, hyphal characteristics, similar radial growth rates, robust growth at 37° C., more or less identical sporulating structures and because both originated from materials collected approximately 80 miles apart in the same geographic area. The sporulating structures of these fungi are extremely reduced and have little morphological complexity. This lack of diagnostic morphology makes identification of these strains, even to a genus, very difficult. The poorly differentiated, simple phialidic conidiogenous cells and brightly colored mycelium are reminiscent of several anamorphic states of fungi in the Hypocreales (Ascomycotina) such as the genus Acremonium, Verticillium, or the microconidial states of some -Fusarium and Cylindrocarpon species. However, the absence of abundant, regularly divergent conidiophores precludes assignment to of the strains to the genus Acremonium. The strains lack the typical verticillate or whorled conidiophore arrangement of Verticillium. The abscence of a macroconidial state prevents assignment of the strains to Fusarium or Cylindrocarpon.

Although both strains are considered to be the same morphological species, they apear to be distinct from each other based on the amount of pigmentation, mycelial exudate, and amount of aerial hyphae as summarized below.

| Colony Characteristics on Czapek Yeast Autolyzateagar | | | |
|---|---|---|---|
| Strain | Pigmentation | Exudates | Aerial Hyphae |
| MF5810 | light vinaceous | sparse | abundant, robust |
| MF5811 | dark vinaceous | copious | moderate |

Also the two strains appear to belong to two different vegetative compatibility groups. Intraspecific pairing of isolates in culture can reveal the genetic diversity of isolates originating from spatially discontinuous locations (A. D. M. Rayner. 1991. The phytopathological significance of mycelial individualism. Annual Review of Phytopathology 29:305–323). Two mm by 3 mm rectangles from the growing edges of mycelial cultures of MF5810 and MF5811 were placed 2 cm apart on malt agar plates (Difco Laboratories). Plates (2 replicates for each pairing) were incubated at 25° C., 12 hr photoperiod and the result of the interactions was assessed after 1 week. Two kinds of interactions resulted. 1) Colonies intermingled with subsequent colony fusion (MF5810 X MF5810; MF581 I X MF5811) and therefore it can be concluded that each of the isolates were somatically (vegetatively) compatible and genetically identical with itself (i.e. self recognition). 2) Or formation of an interaction zone where fusion of opposing colonies failed and which was accompanied by hyphal accumulation at the juncture between opposing colonies and formation of a discrete vinaceous interaction line in agar beneath the colonies which was visible from the reverse of the plates (MF5810 X MF5811), indicating that the isolates were somatically (vegetatively) incompatible (nonself rejection) and thus genetically distinct from each other.

In general the compound structural formula I can be produced by culturing (fermenting) either of the above described strains, MF5810 or MF5811, in an aqueous nutrient medium containing assimilable carbon and nitrogen sources preferably under submerged aerobic conditions, and shaking the culture under constant fluorescent light until a substantial amount of compound of structural formula I is detected in the fermentation broth. The culture is incubated in a aqueous medium at a temperature between 16° C. and 37° C., preferably 25° C. for a period of time necessary to complete the formation of compound structural formula I usually for a period between 3 to 28 days, preferably between 14 to 18 days on a rotary shaker operating at 220 rpm. with a 5 cm throw. The aqueous production medium is maintained at a pH between 5 and 8, preferably about 6.0, at the initiation and termination (harvest) of the fermentation process. The desired pH may be maintained by the use of a buffer such as [2-(N-morpholino)ethanesulfonic acid] monohydrate (MES), 3-(N-morpholino)propanesulfonic acid (MOPS), phosphate buffer and the like, or by choice of nuturient materials which inherently possess buffering properties, such as production media described herein below. Extracting the active compound from the mycelial growth of the culture is preferably done with methyl ethyl ketone (MEK) or with a suitable solvent, concentrating the solution containing the desired compound, then subjecting the concentrated material to chromatographic separation to isolate compound structural formula I from the cultivation medium.

The preferred sources of carbon in the nutrient medium include glucose, sucrose, mannitol, glycerol, xylose, galactose, fructose, lactose, sorbitol, starch, dextrin, other sugars and sugar alcohols, starches and other carbohydrates, or carbohydrates derivatives, and the like. Other sources which may be included are maltose, rhanmose, raffinose, arabinose, mannose, salicin, sodium succinate, acetate, and the like as well as complex nutrients such as oat flour, yellow corn meal, millet, rice, cracked corn, and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium.

The preferred sources of nitrogen are yeast extract, yellow corn meal, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids such as methionine, phenylalanine, serine, alanine, proline, glycine, arginine or threonine, and the like. The various sources of nitrogen can be used alone or in combination in amounts ranging from 0.2 to 10 percent by weight of the medium.

The carbon and nitrogen sources, though advantageously employed in combination, need not be used in their pure form because less pure materials which contain traces of growth factors and considerable quantities of mineral nutrients are also suitable for use. When desired, there may be added to the medium inorganic salts, sodium, potassium, magnesium, calcium, phosphate, sulfate, chloride, carbonate, and like ions which can be incorporated in the culture medium as sodium or calcium carbonate, sodium or potassium phosphate, sodium or potassium chloride, sodium or potassium iodide, magnesium salts, copper salts, cobalt salts, and the like. Also included are trace metals such as cobalt, manganese, iron, molybdenum, zinc, cadmium, copper, and the like. The various sources of inorganic salts can be used alone or in combination in amounts ranging from 0.1 to 1.0, and trace elements ranging from 0.001 to 0.1 percent by weight of the medium.

If necessary, especially when the culture medium foams seriously, a defoaming agent, such as polypropylene glycol 2000 (PPG-2000), liquid paraffin, fatty oil, plant oil, mineral oil or silicone may be added.

Submerged aerobic fermentation conditions are preferred for the production of the compound of structural formula I in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of structural formula I. Accordingly, it is desirable first to produce a vegetative inoculum of the organism by inoculating a relatively small quantity of culture medium with mycelia fragments of the organism produced in a "slant" and culturing said inoculated medium, also called the "seed medium", and then to transfer the cultured vegetative inoculum aseptically to large tanks. The seed medium, in which the inoculum is produced, may be seen in table 1 and is generally autoclaved to sterilize the medium prior to inoculation. The seed medium is generally adjusted to a pH between 5 and 8, preferably about 6.8, prior to the autoclaving step by suitable addition of an acid or base, preferably in the form of a buffering solution. Growth of the culture in this seed medium is maintained between 20° C. and 37° C., preferably 25° C. Incubation of culture MF5810 or MF5811 in seed medium table I is usually conducted for a period of about 2 to 6 days, preferably 3 to 4 days, on a rotary shaker operating at 220 rpm with a 5 cm throw; the length of incubation time may be varied according to fermentation conditions and scales. If appropriate, a second stage seed fermentation may be carried out in the seed medium table I for greater production of mycelial mass by inoculating fresh seed medium with a portion of the culture growth and then incubating under similar conditions but for a shortened period. The resulting growth then may be employed to inoculate the production medium. Agitation and aeration of the culture mixture may be accomplished in a variety of ways. Agitation may be provided by a propeller or similar mechanical agitation equipment, by revolving or shaking within the fermentor, by various pumping equipment or by the passage of sterile air through the medium. Aeration may be effected by passing sterile air through the fermentation mixture.

Preferred seed and production media for carrying out the fermentation for the production of the compound of structural formula I:

TABLE 1

| Seed Medium | | | |
|---|---|---|---|
| | per liter | Trace Element Mix | per liter |
| Corn Steep Liquor | 5 g | $FeSO_4.7H_2O$ | 1 g |
| Tomato Paste | 40 g | $MnSo_4.4H_2O$ | 1 g |
| Oat flour | 10 g | $CuCl_2.2H_2O$ | 25 mg |
| Glucose | 10 g | $CaCl_2$ | 100 mg |
| Trace Element Mix | 10 ml | $H_3BO_3$ | 56 mg |
| | | $(NH_4)_6Mo_7O_{24}.4H_2O$ | 19 mg |
| | | $ZnSo_4.7H_2O$ | 200 mg |
| pH = 6.8 | | | |

TABLE 2

| Production Medium 1 | |
|---|---|
| Component | per liter |
| Yellow Corn Meal | 50 g |
| Yeast Extract | 1 g |
| Glucose | 40 g | no pH adjustment

TABLE 3

| Production Medium 2 | |
|---|---|
| Component | per liter |
| Yellow Corn Meal | 50 g |
| Yeast Extract | 1 g |
| Sucrose | 40 g | no pH adjustment

TABLE 4

| Production Medium 3 | |
|---|---|
| Component | per liter |
| Yellow Corn Meal | 50 g |
| Yeast Extract | 1 g |
| Mannitol | 40 g | no pH adjustment

TABLE 5

| Production Medium 4 | |
|---|---|
| Component | per liter |
| Yellow Corn Meal | 50 g |
| Yeast Extract | 1 g |
| Glycerol | 40 g | no pH adjustment

The product of this invention can be recovered from the culture broth by conventional means which are commonly used for the recovery of other known biologically active substances.

The compound of structural formula I is found in the culture broth. The broth is extracted with an equal volume of methyl ethyl ketone (MEK). The MEK extract is evaporated to dryness and the same solid residue which is obtained is triturated with methylene chloride. The methylene chloride soluble portion is concentrated down and column chromatographed on silica gel using a methylene chloride - ethyl acetate mixture as the eluant. The final purification can be achieved by high pressure liquid chromatography on a reverse phase column eluting with aqueous acetonitrile.

The compound of this invention forms salts with various inorganic and organic acids and bases which are also within the scope of the invention. Such salts include ammonium salts, alkai metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic.

The salts can be formed by conventional means, such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Suitable formations of the compound of this invention may also include conventional pharmaceutically acceptable biolabile esters such as acetate, formed via the hydroxyl group on the pyrrolone.

Endothelin (ET-1), and two closely related bioactive peptides, ET-2 and ET-3, are widely distributed in mammalian tissues, and they can induce numerous biological responses in non-vascular as well as vascular tissues by binding to at least two distinct endothelin receptor subtypes. In addition to smooth muscle, neural and atrial sites, endothelin receptors may be found in gastrointestinal, kidney, lung, urogenital, uteral and placental tissues.

Endothelin is a potent vasoconstrictor peptide and thus plays an in vivo role in arterial pressure-volume homeostasis. Not only peripheral, but coronary vascular resistance as well, is increased by endothelin. Cardiac output is decreased, while plasma renin activity is increased. There is a reduction in renal blood flow and glomerular filtration rate, while levels of atrial natriuretic factor, vasopressin, and aldosterone become elevated.

It is also considered, in accordance with the present invention, that antagonists for the endothelin receptor may be useful in preventing or reducing restenosis subsequent to denudation following angioplasty. Such denudation results from myointimal thickening following angioplasty, which is caused by increased endothelin release. Endothelin acts as a growth factor with respect to smooth muscle and fibroblastic cells, and possibly other types of cells, as well.

Endothelin is also a neuropeptide, acting on the posterior pituitary, where it modulates the release of the neurosecretory hormones vasopressin and oxytocin. Endothelin released from the posterior pituitary also acts as a circulating hormone, having a wide range of actions as discussed further above. This includes effects on the endocrine system, especially the adrenal glands. Endothelin increases plasma levels of epinephrine.

Consequently, the novel compound of the present invention, which is a receptor antagonist of endothelin, has therapeutic usefulness in preventing, decreasing or modulating the various physiological effects of endothelin discussed above, by wholly or partially blocking access of endothelin to its receptor.

Endothelin Receptor Binding Assays

The binding of the novel compound of this invention to the endothelin receptor was determined in accordance with the assay described in detail immediately below. It is similar to the assay described in Arebar et al. (1989) Biochem. Biophys. Res. Commun. 158, 195–201; and Kloog et al. (1989) FEBS Letters, 253, 199–202.

The endothelins (ETs) have a number of potent effects on a variety of cells, and exert their action by interacting with specific receptors present on cell membranes. The compound described in the present invention acts as an antagonist of ET at the receptors. In order to identify ET antagonists and determine their efficacy in vitro, the following three ligand receptor assays were established.

Receptor binding assay using cow aorta membrane preparation

Thoracic aortae were obtained from freshly slaughtered calves and brought to the lab on wet ice. The adventitia were removed, and the aorta was opened up lengthwise. The lumenal surface of the tissue was scrubbed with cheesecloth to remove the endothelial layer. The tissue was ground in a meat grinder, and suspended in ice-cold 0.25M sucrose, 5 mM tris-HCl, pH 7.4, containing 0.5 $\mu$g/mL leupeptin and 7 $\mu$g/mL pepstatin A. Tissue was homogenized twice and then centrifuged for 10 minutes at 750$\times$g at 4° C. The supernatant was filtered through cheesecloth and centrifuged again for 30 minutes at 48,000$\times$g at 4° C. The membrane pellet thus obtained was resuspended in the buffer solution described above (including the protease inhibitors), and aliquots were quick-frozen and stored at $-70°$ C. until use. Membranes were diluted into 50 mM KPi, 5 mM EDTA pH 7.5 containing 0.01% human serum albumin. Assays were done in triplicate. Test compounds and 100 $\mu$M [$^{125}$I]-endothelin-1 (2000–2200 Ci/$\mu$mole, obtained from New England Nuclear or Amersham) were placed in a tube containing this buffer, and the membranes prepared above were added last. The samples were incubated for 60 min at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compound as ET antagonist.

Receptor binding assay using rat hippocampal membrane preparation

Rat hippocampi were obtained from freshly sacrificed male Sprague-Dawley rats and placed in ice cold 0.25M sucrose, 5 mM tris-HCl, pH 7.4 containing 0.5 μg/mL leupeptin, 7 μg/mL pepstatin A. Hippocampi were weighed and placed in a Dounce homogenizer with 25 volumes (wet weight to volume) ice-cold sucrose buffer in the presence of protease inhibitors. Hippocampi were homogenized using the Dounce (glass-glass) homogenizer with type A pestle, with the homogenizer immersed in ice. Tissue homogenate was centrifuged at 750×g for 10 min at 4° C. Supernatant was filtered through dampened cheesecloth, and centrifuged again at 48,000×g for 30 min at 4° C. Membrane pellets were resuspended in sucrose buffer with protease inhibitors. Aliquots of this preparation were quick frozen and stored at −70° C. until use. Membranes were diluted into 50 mM KPi, 5 mM EDTA pH 7.5 containing 0.01% human serum albumin. Assays were done in triplicate. Test compounds and 25 pM [$^{125}$I]-endothelin-1 (2000-2200 Ci/μmole, obtained from New England Nuclear or Amersham) were placed in a tube containing this buffer, and the membranes prepared above were added last. The samples were incubated for 60 rain at 37° C. At the end of this incubation, samples were filtered onto prewetted (with 2% BSA in water) glass fiber filter pads and washed with 150 mM NaCl, 0.1% BSA. The filters were assayed for $^{125}$I radioactivity in a gamma counter. Nondisplaceable binding of [$^{125}$I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [$^{125}$I]-endothelin-1 was presented as a measure of the potency of such compounds as endothelin antagonists.

Receptor binding assay using cloned human ET receptors expressed in Chinese Hamster Ovary Cells Both endothelin receptor subtypes were cloned from a human cDNA library and were individually expressed in Chinese Hamster Ovary cells. Cells were harvested by addition of 126 mM NaCl, mM KCl, 2 mM EDTA, 1 mM NaH$_2$PO$_4$, 15 mM glucose, 10 mM tris/HEPES pH 7.4 Cells were centrifuged at 250×g for 5 minutes. The supernatant was aspirated off, and the cells were resuspended in the 50 mM KPi, 5 mM EDTA pH 7.5 containing 0.01% human serum albumin. Assays were done in triplicate. Test compounds and 25-100 pM [$^{125}$I]-endothelin-1 (2000-2200 Ci/μmole, obtained from New England Nuclear or Amersham) were placed in a tube containing 50 mM KPi, 5 mM EDTA pH 7.5 containing 0.01% human serum albumin, and the cells prepared above were added last. The samples were incubated for 60 min at 37° C. At the end of this incubation, samples were filtered onto prewetted (with 2% BSA in water) glass fiber filter pad and washed with 150 mM NaCl, 0.1% BSA.

The filters were assayed for $^{125}$I radioactivity in a gamma counter. Nondisplaceable binding of [125I]-endothelin-1 was measured in the presence of 100 nM unlabelled endothelin-1 [Endothelin-1 (ET-1) was purchased from Peptides International (Louisville, Ky.)]. Specific binding is defined as total binding minus nondisplaceable binding. The inhibitory concentration (IC$_{50}$) which gives 50% displacement of the total specifically bound [125I]-endothelin-1 was presented as a measure of the potency of such compounds as endothelin antagonists.

The binding assays described above were used to evaluate the potency of interaction of the compound of the invention with endothelin receptors. To determine whether this compound was an endothelin antagonist, assays which measure the ability of the compound to inhibit endothelin-stimulated phosphatidylinositol hydrolysis were established. Rat uterus contains predominantly one of the known endothelin receptor subtypes (ET$_A$).

Phosphatidylinositol hydrolysis assays using rat uterine slices

Diethylstilbestrol primed female Sprague-Dawley rats were sacrificed and their uteri were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 μM myo-[$^3$H]-inositol (Amersham) was added. The mince was incubated 120 min at 37° C., with constant oxygenation. After incubation, the loaded tissue mince was washed five times with the same oxygenated buffer to remove excess radiolabelled inositol. The tissue mince was resuspended in the above buffer, containing 10 mM LiCl, aliquotted into tubes, and 3 mM endothelin-1 with and without test compounds was added to a final concentration of 3 nM to start the assay. Assays were done in quadruplicate. Samples were incubated at 37° C. under blowing O$_2$ in a hooded water bath for 30 minutes. Reaction was stopped by addition of trichloroacetic acid to 6% concentration. Samples were sonicated for 10 min, centrifuged 20 min, then trichloroacetic acid was extracted with water-saturated ethyl ether. An aliquot of each sample was neutrallized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 nM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence on endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Sarafotoxin S6c is a member of the endothelin family which binds preferentially to one of the known endothelin receptor subtypes (ET$_B$).

Phosphatidylinositol hydrolysis assays using rat lung slices

Male Sprague-Dawley rats were sacrificed and their lungs were collected, dissected of fat and connective tissue and minced. Minced tissue was added to oxygenated (95% O$_2$, 5% CO$_2$) 127 mM NaCl, 25 mM NaHCO$_3$, 10 mM Glucose, 2.5 mM KCl, 1.2 mM KH$_2$PO$_4$, 1.2 mM MgSO$_4$, 1.8 mM CaCl$_2$. To the tissue mince, 1.2 μM myo-[$^3$H]-inositol was added. The mince was incubated 60 min at 37° C., with constant oxygenation. After incubation, loaded tissue mince was washed five times with the same oxygenated buffer to remove excess radiolabelled inositol. Tissue mince was resuspended in the above buffer, containing 10 mM LiCl, aliquotted into tubes, and sarafotoxin S6c (to a final concentration of 3 nM) with and without test compounds was added to start the assay. Assays were done in quadruplicate. Samples were incubated at 37° C. under blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence on sarafotoxin minus the values in the absence of sarafotoxin (basal). Test sample values are the values in the presence of sarafotoxin and test sample minus basal. Inhibitory concentration (IC$_{50}$) is the concentration of test compound required to give a sample activity of 50% of control value.

Phosphatidylinositol hydrolysis assays using cloned human endothelin receptors expressed in Chinese Hamster Ovary cells Endothelin receptors of both receptor subtypes were cloned from a human cDNA library and were individually expressed in Chinese Hamster Ovary cells. Cells were loaded overnight by the addition of 1.2 μM myo-[$^3$H]-inositol to their growth medium. Cells were harvested by addition of 126 mM NaCl, 5 mM KCl, 2 mM EDTA, 1 mM NaH$_2$PO$_4$, 15 mM glucose, 10 mM tris-/HEPES pH 7.4 Cells were washed five times by centrifugation at 250×g for 5 minutes to remove excess radiolabelled inositol. The supernatant was aspirated off, and the cells were resuspended in the same oxygenated (95% O$_2$, 5% CO$_2$) buffer containing 10 mM LiCl, aliquotted into tubes, and endothelin-1 (to a final concentration of 0.3 nM) with and without test compounds was added to start the assay. Assays were done in quadruplicate. Samples were incubated at 37° C. tinder blowing O$_2$ in a hooded water bath for 30 minutes. Reaction was stopped by addition of 0.5 mL 18% trichloroacetic acid to 6% concentration. Samples were sonicated for 10 min, centrifuged 20 min, then trichloroacetic acid was extracted with water-saturated ethyl ether. An aliquot of each sample was neutralized and diluted by addition of 50 mM tris-HCl pH 7.4. A 100 μL aliquot of this solution was assayed for radioactivity in a beta counter. The diluted neutralized sample was applied to Dowex 1×8-formate columns, washed with water, then washed with 60 mM ammonium formate, 5 mM sodium tetraborate. Samples were eluted with 200 mM ammonium formate, 5 mM sodium tetraborate. The radioactivity of each eluted sample was measured in a beta counter. Radioactivity was normalized by dividing radioactivity in post column sample by radioactivity in precolumn sample. Control values (100% stimulated) are values in the presence of endothelin minus the values in the absence of endothelin (basal). Test sample values are the values in the presence of endothelin and test sample minus basal. Inhibitory concentration (IC$_{50}$) is the concentration of test compound required to give a sample activity of 50% of control value.

Using the methodology described above, the compound of the invention was evaluated and found to exhibit IC$_{50}$ values of at least <50 μM thereby demonstrating and confirming the utility of the compound of this invention as an effective endothelin antagonist.

Accordingly the novel compound of the present invention is useful in human therapy for treating asthma, hypertension, pulmonary hypertension, arterioscelerosis, congestive heart failure, renal failure, particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, by adminstration to a patient in need of such treatment of a therapeutically effective amount thereof.

In the management of hypertension and the clinical conditions noted above, the compound of this invention may be utilized in compositions such as tablets, capsules or elixirs for oral administration, suppositories for rectal administration, sterile solutions or suspensions for parenteral or intramuscular administration, and the like. The compound of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 200 mg. per patient per day which can be administered in single or multiple doses. Preferably, the dosage range will be about 50 to 100 mg. per patient per day; more preferably about 0.5 to 100 mg. per patient per day.

The present invent ion also relates to pharmaceutical compositions for treating asthma, hypertension, pulmonary hypertension, arterioscelerosis, congestive heart failure, renal failure particularly post-ischemic renal failure, cyclosporin nephrotoxicity, vasospasm, vascular restenosis, cerebral and cardiac ischemia and other ischemic states, myocardial infarction, Raynaud's disease, inflammatory bowel diseases, including Crohn's disease and ulcerative colitis, as well as other inflammatory diseases, or endotoxic shock caused by or associated with endothelin, comprising a therapeutically effective amount of the novel compound of this invention together with a pharmaceutically acceptable carrier therefor.

About 1 to 100 mg. of compound of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples illustrate the processes for the preparation of the compound of Formula I and their incorporation into pharmaceutical compositions and as such are not to be considered as limiting the invention set forth in the claims appended hereto.

EXAMPLE I

Fermentation Conditions For Production of Structural Formula I Using Cultures MF5810 or MF5811

Step 1: Seed Culture

Vegetative mycelia of the culture were prepared by inoculating 54 ml of seed medium (Table 1) in a 250 ml unbaffled Erlenmeyer flask with 2-ml of mycelia in 10% glycerol (MF5810, ATCC 74201 or MF5811, ATCC 74202) that had been stored at −80° C. Seed cultures were incubated for 3 days at 25° C. and 50% relative humidity on a rotary shaker with a 5-cm throw at 220 rpm in a room with constant fluorescent light.

Step 2: Production Conditions

Two-ml portions of the seed culture were used to inoculate 50-ml portions of liquid production medium 1 (Table 2) in 250 ml unbaffled Erlenmeyer flasks. These cultures were incubated at 25° C., 220 rpm with 50% relative humidity in a room with constant fluorescent light. Maximal production of the compound of Structural Formula I in the production medium 1 occured by day 18 (MF5811); 66 mg/L. At harvest, the compound of Structural Formula I was extracted from the culture broth with an equal volume of methyl ethyl ketone (50 ml per 250 ml flask and shaken at 220 rpm for 1 hour at 25° C). It was determined that cultures MF5810 and MF5811 were also capable of producing structural formula I in production medium 2, 3 and 4 (Tables 3, 4 and 5). The nutrient media described herein are merely examples of the types of media that may be employed and are not intended to be limiting.

Step 3: Analytical Procedure used to monitor the production of the compound of Structural Formula I in fermentation samples Analytical procedures were used to monitor production in fermentation samples. The method used consisted of extracting whole broth with 1.4 volumes of methyl ethyl ketone and evaporating the solvent. High pressure liquid chromatography analyses were performed on 10 μL aliquots of acetonitrile-soluble portion of the extracts, obtained by the extensive trituration of the semi-solid residue with one/fifth the original volume of acetonitrile. Whatman Partisil 50DS-3 column maintained at 40° C. and eluted at 1 mL per minute with 75% aqueous acetonitrile, K'=4.9; detection at UV 220 nm afforded a linear response from 0.1 to 6 micrograms per injection.

The culture was thus determined to reproducibly be capable of producing:

a. 21 mg per liter in production medium 1
b. 12 mg per liter in production medium 2
c. 40 mg per liter in production medium 3
d. 23 mg per liter in production medium 4.

EXAMPLE 2

An 18-flask fermentation batch prepared as in Example 1 was extracted with methyl ethyl ketone (50 ml per flask, stirring for one hour). After evaporation to dryness under reduced pressure, the semisolid residue obtained was triturated with 300 ml of methylene chloride, which afforded a biologically active extract; the inactive solids remaining could be filtered off and discarded.

The methylene chloride-soluble portion from above was first concentrated to 20 ml then applied onto a 75 ml E. Merck silica gel 60 (230–400 mesh) column packed in and equilibrated with methylene chloride. The adsorbent was washed in sequence with methylene chloride containing increasing amounts of ethyl acetate, then with ethyl acetate containing 0, 5, 10 and 20% v/v methanol. All the biological activity was found in the methylene chloride - ethyl acetate 1:1 washings (100 mg of oily residue upon evaporation of the solvent), which were further processed by preparative thin layer chromatography (TLC) on E. Merck silica gel 60F 254 plates using a mixture of methylene chloride - methanol - concentrated ammonia 95:5:0.5, v/v/v.

The single active fraction thus obtained was dissolved in 0.4 ml of dimethyl sulfoxide - methanol 1:1 and finally purified by preparative high performance liquid chromatography (HPLC) at room temperature on a 25 cm long Whatman Partisil 10 ODS-3 Magnum-9 column eluted at 4 ml per minute with a 40-minute gradient of 60% aqueous acetontirile to 100% acetonitrile. Although more than one peak of bioactivity was obtained, all but the major component were determined to be artifacts of the purification procedure. The major active compound was present in fractions corresponding to 4.25 to 5 column volumes of eluate.

Its homogeneity was ascertained by NMR spectroscopy, TLC in several normal phase and reverse phase systems and by HPLC (Whatman Partisil 50DS-3, 4.6×25 cm column maintained at 40° C. and eluted with 75% aqueous acetonitrile delivered at 1 ml per minute): k'=4.9.

EXAMPLE 3

The instability of the product was attributed to its sensitivity to methanol particularly at a pH below 6. An improved purification process avoided the use of methanol as described in this Example.

A fifteen-flask fermentation batch, prepared as detailed in Example 1, using the MF5810 culture, was thus extracted with methyl ethyl ketone. After evaporation of the solvent and extensive trituration with methylene chloride as before, purification proceeded via repeated column chromatography steps on silica gel 60 using methylene chloride ethyl acetate mixtures; final purification could be achieved by HPLC (Whatman Partisil 10 ODS-3 25 cm Magnum 9 column eluted at room temperature with 4 ml per minute 60% aqueous acetonitrile; volume of retention 96–108 ml). Yield 15 mg, corresponding to 85% recovery from broth.

EXAMPLE 4

Culture MF5811 proved to be a richer source of the compound of Structural Formula I. A fermentation batch of this organism, containing some 70 mg was processed as described in Example 3. This procedure afforded 63 mg of homogeneous material (90% yield).

Nuclear Magnetic Resonance Spectra $^1$H-NMR in $CD_2Cl_2$ ($\delta$) at 500 MHz: 0.86 (3H, d, J=7 Hz), 0.90 (3H, s), 0.96 (1H, m), 0.98 (2H, m), 1.46 (3H, m), 1.49 (3H, d, J=1 Hz), 1.50 (1H, m), 1.61 (3H, s), 1.62 (3H, brd, J=8 Hz), 1.64 (1H, m), 1.70 (1H, m), 1.73 (1H, m), 1.76 (1H, dr, J=11, 2.5 Hz), 3.05 (1H, d, J=13.5 Hz), 3.10 (1H, brd J=8 Hz), 3.17 (1H, d, J=13.5 Hz), 3.72 (1H, dd, J=12, 8 Hz), 5.20 (1H, q, J=6.5 Hz), 5.40 (1H, brs), 5.46 (1H, brs), 6.18 (1H, brs), 7.23 (1H, brs), 7.25 (2H, m), 7.30 (1H, m), 7.33 (2H, m), 7.40 (1H, d, J=2.0 Hz).

$^{13}$C-NMR in $CD_2Cl_2$($\delta$) at 125 MHz: 13.62 ($CH_3$), 15.09 ($CH_3$), 16.56 ($CH_3$), 20.63 ($CH_3$), 22.04 ($CH_3$), 22.92 ($CH_3$), 24.70 ($CH_2$), 27.79 (CH), 35.35 (qC), 36.10 ($CH_2$), 40.29 (CH), 43.80 ($CH_2$), 48.77 ($CH_2$), 50.24 (CH), 51.37 (CH), 86.03 (qC), 124.67 (CH), 127.7 (CH), 128.8 (2×CH), 130.00 (qC), 130.80 (2×CH), 133.81 (CH), 134.13 (qC), 134.76 (qC), 135.80 (qC), 136.82 (qC), 136.98 (CH), 154.30 (CH), 167.76 (CO), 196.3 (CO).

Fast Atom Bombardment Mass Spectrometry

The FAB mass spectrum was unusual in that a peak that appeared to have arisen from an adduct ion incorporating a matrix molecule [[487+DTT/DTE+Li]$^+$ at m/z 648] was three times stronger than peaks originating from either the simple protonated or lithiated adducts. Identification of a MW 487 component was supported by the appearance of a strong molecular ion at m/z 487 in the EI mass spectrum. The molecular ion was peak-matched: found 487.3059, calculated for $C_{32}H_{41}$ $NO_3$ 487.3086.

A key fragment ion at m/z 271 was peak-matched: found 271.2424, calculated for $C_{20}H_{31}$ 271.2426.

What is claimed is:

1. A compound of structural formula I:

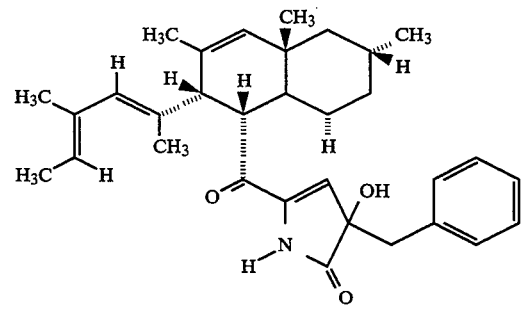

or a pharmaceutically acceptable salt selected from the group consisting of the sodium salt, potassium salt, calcium salt, magnesium salt, dicyclohexylamine salt, N-methyl-D-glucamine salt, salt with arginine, salt with lysine, HCl salt, HBr salt, $H_2SO_4$ salt, $H_3PO_4$ salt, methanesulfonic acid salt, toluenesulfonic acid salt, maleic acid salt, fumaric acid salt camphorsulfonic acid salt.

* * * * *

UNITED STATES PATENT AND TRADEMARK OFFICE
CERTIFICATE OF CORRECTION

PATENT NO. : 5,352,800
DATED : October 4, 1994
INVENTOR(S) : G.F. Bills, et. al.

It is certified that error appears in the above-indentified patent and that said Letters Patent is hereby corrected as shown below:

On the cover page, in box [75] entitled "Inventors", Gerard F. Bills should read Gerald F. Bills.

Signed and Sealed this

First Day of August, 1995

Attest:

BRUCE LEHMAN

*Attesting Officer*   *Commissioner of Patents and Trademarks*